United States Patent
Merritt

(10) Patent No.: US 10,212,945 B1
(45) Date of Patent: Feb. 26, 2019

(54) METHOD OF MAKING A MOSQUITO REPELLANT COMPOSITION

(71) Applicant: John Merritt, Latrobe, CA (US)

(72) Inventor: John Merritt, Latrobe, CA (US)

( * ) Notice: Subject to any disclaimer, the term of this patent is extended or adjusted under 35 U.S.C. 154(b) by 0 days.

(21) Appl. No.: 15/860,805

(22) Filed: Jan. 3, 2018

(51) Int. Cl.
- *A01N 65/00* (2009.01)
- *A01N 31/02* (2006.01)
- *A01N 37/04* (2006.01)
- *A01N 61/02* (2006.01)

(52) U.S. Cl.
CPC .............. *A01N 65/00* (2013.01); *A01N 31/02* (2013.01); *A01N 37/04* (2013.01); *A01N 61/02* (2013.01)

(58) Field of Classification Search
None
See application file for complete search history.

(56) References Cited

U.S. PATENT DOCUMENTS

| | | | |
|---|---|---|---|
| 6,623,766 B1 * | 9/2003 | Tripathi | A01N 65/00 424/742 |
| 2008/0274072 A1 * | 11/2008 | Manolas | A61L 9/012 424/76.9 |
| 2017/0295801 A1 * | 10/2017 | Waite | A01N 65/00 |

* cited by examiner

*Primary Examiner* — Susan Hoffman

(57) ABSTRACT

A method of making a mosquito repellant composition which includes a composition of lemon balm leaves, water, antimicrobial preservative, alcohol free witch hazel, sodium lactate, camelina oil, mineral oil, cetyl alcohol, steric acid, fragrance and titanium dioxide.

2 Claims, No Drawings

METHOD OF MAKING A MOSQUITO REPELLANT COMPOSITION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to mosquito repellants and more particularly pertains to a new mosquito repellant for placing on a person or articles to repel mosquitos.

BRIEF SUMMARY OF THE INVENTION

An embodiment of the disclosure meets the needs presented above by a composition that includes lemon balm leaves, water, antimicrobial preservative, alcohol free witch hazel, sodium lactate, camelina oil, mineral oil, cetyl alcohol, steric acid, fragrance and titanium dioxide.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

Not Applicable

DETAILED DESCRIPTION OF THE INVENTION

A new mosquito repellant embodying the principles and concepts of an embodiment of the disclosure will be described.

A method of making a mosquito repellant composition generally comprises the steps of:

A. Preparing a first solution which includes the steps of:
   1) Cutting 60 grams of fennel plant (*Foeniculum vulgare*) into pieces has a length between 0.7 inches and 1.3 inches;
   2) cutting at least 4 lemon balm leaves (*Melissa officinalis*);
   3) putting the fennel plant and the lemon balm leaves into between 0.40 liters and 0.50 liters of water;
   4) boiling the water, fennel plant and lemon balm leaves for between 30 minutes and 60 minutes;
   5) letting the water cool to between 42° C. and 45° C. within a container.
   6) adding 2.5 ml an antimicrobial preservative to the container;
   7) sealing the container and agitating the container;
   8) storing the container for between 7 days and 9 days at a temperature of between 19° C. and 23° C. and agitating the container two times a day while the container is being stored;
   9) after the storage period has ended, straining the water to remove the lemon balm leaves and the fennel plant:
   10) adding to the water adding between 0.08 liters and 0.10 liters alcohol free witch hazel; and
   11) adding to the water between 5.0 ml and 7.0 ml of sodium lactate (typically found as a 60% concentration).

B. Preparing a second solution which includes the mixing together of:
   1) between 28.0 ml and 32.0 ml camelina oil;
   2) between 28.0 ml and 32.0 ml mineral oil;
   3) between 16.0 ml and 19.0 ml cetyl alcohol (sold typically as flakes); and
   4) between 16.0 ml and 19.0 ml steric acid (typically sold as a powder or flakes).

C. Heating the first solution and the second solution separately from each other for between 6 minutes and 8 minutes at a temperature of between 75° C. and 78° C.

D. Adding the first and second solutions together and mix well for at least 2.0 minutes to define a mixture.

E. Cooling the mixture to less than 45° C.

F. Adding to the mixture to define a final composition:
   1) between 8.0 ml and 12.0 ml of antimicrobial preservative;
   2) between 14.0 ml and 16.0 ml of aloe fragrance (ubiquitously found by multiple retailers); and
   3) between 14.0 ml and 16.0 ml of titanium dioxide (typically sold as a powder and measured herein by volume of such).

G. Pouring the final composition into a dispensing bottle.

In the above composition, the antimicrobial preservative may comprise a composition of Propylene Glycol, Diazolidinyl Urea and) Iodopropynyl Butylcarbamate. More particularly, this composition may be purchased under the tradename Liquid Germall sold by Ashland Global Holdings Inc., 50 East River Center Blvd., Covington, Ky. The alcohol free witch hazel may come from any retail source such as is sold by Hawaii Pharm, 1154 Keeaumoku St., Honolulu, Hi. The mineral oil may comprise any readily available mineral oil such as Nature's Oil mineral oil available from Nature's Oil, 125 Lena Drive, Aurora, Ohio, which is also a supplier of camelina oil.

In use, the final composition may be sprayed or rubbed on a person's skin, clothing or other areas where it is desirable to repel mosquitos.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A method of making a mosquito repellant comprising the steps of:
    preparing a first solution including the steps of:
        cutting fennel plant;
        cutting lemon balm leaves;
        putting said fennel plant and said lemon balm leaves into water;
        boiling said water, fennel plant and lemon balm leaves;
        letting said water cool in a container;
        adding an antimicrobial preservative to said container;
        sealing said container and agitating said container;
        storing said container;
        straining said water to remove said lemon balm leaves and said fennel plant;
        adding to said water:
            alcohol free witch hazel;
            sodium lactate;
    preparing a second solution including:
        camelina oil;
        mineral oil;
        cetyl alcohol;
        steric acid;
    heating said first solution and said second solution separately from each other;
    add said first and second solutions together and mix well to define a mixture;
    cool said mixture;
    add to said mixture to define a final composition:
        antimicrobial preservative;
        fragrance;
        titanium dioxide;
    pouring said final composition into a dispensing bottle.

2. A method of making a mosquito repellant comprising the steps of:
    preparing a first solution including the steps of:
        cutting 60 grams of fennel plant into pieces having a length between 0.7 inches and 1.3 inches;
        cutting at least 4 lemon balm leaves;
        putting said fennel plant and said lemon balm leaves into between 0.40 liters and 0.50 liters of water;
        boiling said water, fennel plant and lemon balm leaves for between 30 minutes and 60 minutes;
        letting said water cool to between 42° C. and 45° C. within a container;
        adding 2.5 ml an antimicrobial preservative to said container;
        sealing said container and agitating said container;
        storing said container for 8 days at a temperature of between 19° C. and 23° C. and agitating said container two times a day while said container is being stored;
        straining said water to remove said lemon balm leaves and said fennel plant;
        adding to said water:
            adding between 0.08 liters and 0.10 liters alcohol free witch hazel;
            adding between 5.0 ml and 7.0 ml of sodium lactate;
    preparing a second solution including:
        between 28.0 ml and 32.0 ml camelina oil;
        between 28.0 ml and 32.0 ml mineral oil;
        between 16.0 ml and 19.0 ml cetyl alcohol;
        between 16.0 ml and 19.0 ml steric acid;
    heating said first solution and said second solution separately from each other for between 6 minutes and 8 minutes at a temperature of between 75° C. and 78° C.;
    add said first and second solutions together and mix well for at least 2.0 minutes to define a mixture;
    cool said mixture to less than 45° C.;
    add to said mixture to define a final composition:
        between 8.0 ml and 12.0 ml of antimicrobial preservative;
        between 14.0 ml and 16.0 ml of aloe fragrance;
        between 14.0 ml and 16.0 ml of titanium dioxide;
    pouring said final composition into a dispensing bottle.

* * * * *